United States Patent [19]

Guethlein et al.

[11] Patent Number: 4,985,414
[45] Date of Patent: Jan. 15, 1991

[54] 1-NAPHTHOLPHTHALEIN MONOPHOSPHATES AND DIAGNOSTIC REAGENTS CONTAINING THEM

[75] Inventors: Werner Guethlein, Mannheim; Hartmut Merdes, Heidelberg, both of Fed. Rep. of Germany

[73] Assignee: Boehringer Mannheim GmbH, Mannheim, Fed. Rep. of Germany

[21] Appl. No.: 273,403

[22] Filed: Nov. 18, 1988

[30] Foreign Application Priority Data

Nov. 20, 1987 [DE]  Fed. Rep. of Germany ....... 3739284

[51] Int. Cl.$^5$ .......................... C07C 9/06; C07C 9/28; A01N 57/00; A61K 31/665
[52] U.S. Cl. ..................................... 514/100; 549/220
[58] Field of Search ...................... 549/220, 445, 434; 514/100, 470

[56] References Cited

U.S. PATENT DOCUMENTS

| | | | |
|---|---|---|---|
| 3,331,857 | 7/1987 | Colemar | 260/343.4 |
| 3,331,862 | 7/1987 | Merrill et al. | 260/396 |
| 3,823,071 | 7/1974 | Roy | 549/226 |
| 3,931,228 | 1/1976 | Borror | 549/307 |
| 3,975,405 | 8/1976 | Hamill |  |
| 4,032,545 | 6/1977 | Borror | 549/307 |
| 4,035,391 | 7/1977 | Borror | 549/307 |

OTHER PUBLICATIONS

Roy, "Rapid Method for Determining Alkaline Phosphotase Activity ...", Clin. Chem. 16, 431-6 (1970).

Morin, "Ammonium Thymolphthalein Monophosphate as a New Substitute...", Clin. Chem. 19, 1135-8 (1973). Abstract: Tapaneic Published Pat. Appl. No. 58-158199 (1983).

Primary Examiner—Richard L. Raymond
Assistant Examiner—Raymond Covington
Attorney, Agent, or Firm—Felfe & Lynch

[57] ABSTRACT

New 1-naphtholphthalein monophosphates of the formula

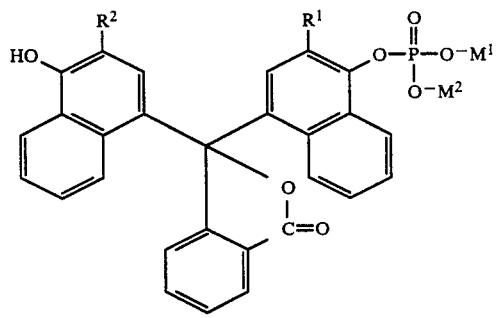

wherein each of $R^1$ and $R^2$ is hydrogen or halogen, and each of $M^1$ and $M^2$ is a proton or an alkali metal, alkaline earth metal, ammonium, dicyclohexylammonium, tetraalkylammonium or alkanolammonium cation, and the tautomeric transformation products thereof, are useful as substrates for detection and photometric determination of alkaline phosphotase.

7 Claims, No Drawings

1-NAPHTHOLPHTHALEIN MONOPHOSPHATES AND DIAGNOSTIC REAGENTS CONTAINING THEM

BACKGROUND OF THE INVENTION

The present invention is concerned with new 1-naphtholphthalein monophosphates and the salts thereof which, as enzyme substrates, form a coloured anion under the influence of esterases at alkaline pH values and especially under the influence of alkaline phosphatase (EC 3.1.3.1). The present invention is also concerned with processes for the preparation of these monophosphates and of the salts thereof, as well as with a process and agent for the detection and photometric determination of alkaline phosphatase.

Alkaline phosphatase (AP) occurs, for example, in the liver, bones, in the small intestine, in the kidneys, in the bile and, to a smaller extent, in the placenta. An increase of the AP activity in the plasma has a diagnostic importance especially for the detection of liver diseases and diseases of the bone skeleton. For example, increased AP levels are observed in the case of Paget's disease, osteosarcomas, jaundice, hepatitis and similar diseases.

Over and above their physiological place value, alkaline phosphatase has, in recent years, achieved importance as a diagnostic adjuvant. Thus, for example, this enzyme is used as an indicator enzyme for enzyme immunoassays.

Thus, clinical chemistry and diagnosis require a method for the quantitative determination of alkaline phosphatase which is simple to use and, at the same time, gives results with good reproducibility. As a rule, for this purpose, there is used the direct photometric or fluorometric determination of compounds which are obtained from added specific substrates by hydrolytic cleavage brought about by AP. The compounds liberated by alkaline phosphatase are chromogenic or mesomerism-stabilised alcohols, especially phenols, and phosphate residues. As a rule, the former are determined qualitatively or quantitatively.

Not only in the case of colorimetric determinations but also in the case of fluorometric determinations, a parallel or subsequent carrying out of a blank value (without sample, i.e. without AP) is advisable in order to be able to recognise interferences due to a possible absorption possibly of unreacted substrate.

Besides p-nitrophenyl phosphate, naphthyl phosphates and phenolphthalein diphosphoric acids and appropriate derivatives thereof, phenolphthalein mono phosphoric acid and the salts thereof can be used as AP substrates (see U.S. Pat. Nos. 3,331,857 and 3,331,862). However, these compounds are unsatisfactory for the determination of alkaline phosphatase especially since the detection of the liberated amount of phenolphthalein is falsified by other compounds present in the sample. Thus, numerous serum components, for example bilirubin, have, like the mentioned phenolates liberated from the AP substrates, an absorption maximum at about 400 to 450 nm.

Therefore, thymolphthalein monophosphoric acid and, because of their good water-solubility, the corresponding sodium and ammonium salts, are today preferably used as substrates for the determination of alkaline phosphatase (see Clin. Chem., 16, 431–436/1970; Clin. Chem., 19, 1135–1138/1973; Japanese Patent Specification No. 83-158,199). In the absorption or emission spectrum, liberated thymolphthalein displays a maximum absorption band at about 595 nm. However, it is a disadvantage in the case of these compounds that, on the one hand, they have an insufficient sensitivity in the case of intestinal and placental AP and, on the other hand, there must be carried out not a kinetic determination but rather an end point determination which includes a rebuffering step.

o-Cresolphthalein monophosphoric acid is a further phenolphthalein derivative which is today commonly used as an AP substrate (see U.S. Pat. No. 3,975,405). With the help of this substrate, there is possible not only a continuous but also a discontinuous determination of alkaline phosphatase since the liberated o-cresolphthalein, unlike thymolphthalein, absorbs in a pH range which is optimum for the AP determination. However, the spectroscopic determination of the liberated o-cresolphthalein is disturbed in the presence of haemolytic samples since the absorption maximum of the o-cresolphthalein anion lies at about 570 nm.

Thus, it is an object of the present invention to provide new substrates for the determination of alkaline phosphatases which, besides a sufficient water-solubility, possess the property of liberating hydrolysis products under the influence of the enzyme. The liberated products have absorption maxima which are as long-waved as possible and thus, in the case of photometric determinations, are not or only slightly influenced by other sample components such as, particularly, haemolysis products. Furthermore, the new AP substrats are to be sufficiently stable and obtainable in high purity by simple and economically interesting syntheses.

This object is achieved by the new 1-naphtholphthalein monophosphates according to the present invention which, under the influence of alkaline esterases and especially of alkaline phosphatases, are reacted to give anions absorbing in the long wavelengths.

SUMMARY OF THE INVENTION

Thus, according to the present invention, there are provided new compounds for the determination of alkaline phosphotase activity and diagnostic agents containing said compounds in a buffered system. The compounds have the general formula:

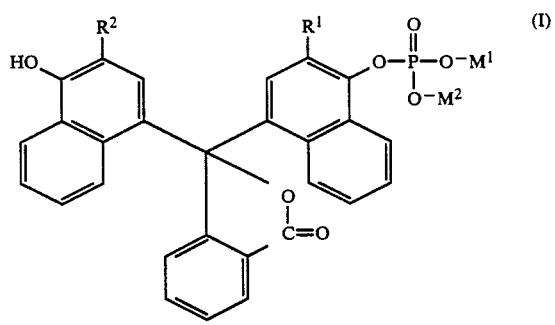

in which $R^1$ and $R^2$, which can be the same or different, are hydrogen or halogen atoms and $M^1$ and $M^2$, which are the same or different, are protons or alkali metal, alkaline earth metal, ammonium, dicyclohexylammonium, tetraalkylammonium or alkanolammonium cations, and the tautomeric transformation products thereof.

DETAILED DISCLOSURE

All the 1-naphtholphthalein monophosphates of general formula (I) are new compounds. They can be prepared from methods known in phenol chemistry.

Preferably, 1-naphtholphthalein and the salts thereof of the general formula:

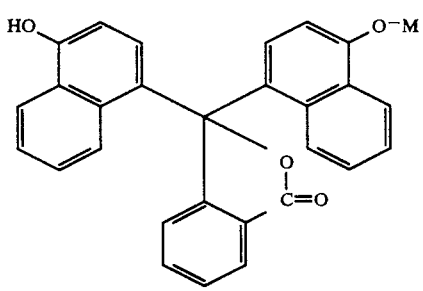
(II)

in which M is a proton or an alkali metal, alkaline earth metal, ammonium, dicyclohexylammonium, tetraalkylammonium or alkanolammonium cation, is reacted in known manner with a phosphorus compound of the general formula:

(III)

in which $R^3$ and $R^4$, which can be the same or different, are halogen atoms or aryl or alkylaryl radicals and $R^5$ is a hydrogen or halogen atom, in the presence of an organic base in an anhydrous solvent or solvent mixture and optionally brominated.

Thus, for example 1-naphtholphthalein mono-phosphates of general formula (I), in which $R^1$ and $R^2$ are hydrogen atoms and $M^1$ and $M^2$ have the above-given meanings, can be reacted with an equimolar amount of phosphorus oxychloride in the presence of 0.93 mole pyridine. There is thereby substantially obtained the desired monophosphate (I), wherein $R^1$ and $R^2$ are hydrogen atoms, besides a little diphosphate and starting material which is removed by shaking out with butanol/ligroin (1/1 v/v) at pH 10.3. The separation of the monophosphate from the diphosphate is achieved by means of column chromatography.

Furthermore, the monophosphates of general formula (I) can be prepared analogously to Coulter's synthesis for o-cresolphthalein monophosphate (see U.S. Pat. No. 3,975,405) by reacting 1-naphtholphthalein and dibenzyl phosphite with carbon tetrachloride in anhydrous tetrahydrofuran in the presence of an organic base, for example triethylamine, to give a dibenzylphosphoric acid ester of the general formula:

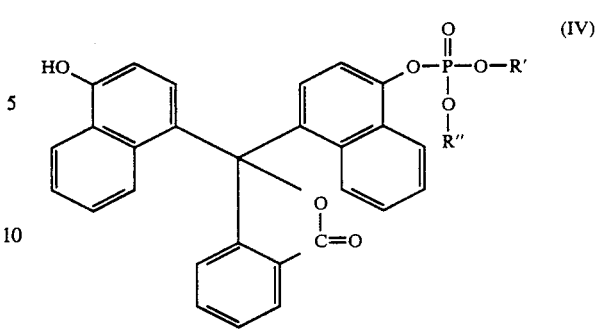
(IV)

wherein R′ and R″ each are benzyl radicals. Compounds of general formula (IV) are purified by column chromatography and debenzylated by catalytically activated hydrogen in the presence of palladium/carbon. After further column chromatographic purification, there are obtained compounds of general formula (I), wherein $R^1$ and $R^2$ are hydrogen atoms.

Furthermore, instead of dibenzyl phosphite, there can be used diphenyl phosphite. There are thus obtained compounds of general formula (IV), wherein R′ and R″ are phenyl radicals. The splitting off of the phenyl radicals can take place with hydrogen in the presence of rhodium/charcoal. 1-Naphtholphthalein can be reacted analogously with diphenylphosphoryl chloride and the protective groups removed by hydrogenation in the presence of a rhodium/charcoal catalyst. In any case, compounds of general formula (I) are obtained.

Furthermore, in the case of the synthesis of monophosphates of general formula (I), the preparation of the dibenzylphosphoric acid ester of general formula (IV) in an aqueous medium by phase transfer catalysis and subsequent catalytic debenzylation analogously to the procedure of A. Zwierzak (*Synthesis*, 1976, 305) has proved to be useful. As phase transfer catalysts, there can be used, for example, quaternary ammonium salts, such as benzyl tributyl ammonium bromide and benzyl triethyl ammonium bromide, phosphonium salts, such as triphenylphosphonium chloride, polyethylene glycols and/or crown ethers and mixtures of the compounds here mentioned by way of example. The removal of the acetic acid adhering after column chromatographic purification is carried out by dissolving the compound in ammonia and applying to an HP-20 absorber column (polystyrene-divinylchlorobenzene resin). After elution with water, isopropanol and ammonia-containing water, there is preponderantly obtained pure monophosphate of general formula (I). The acetic acid can also be removed by the addition of dicyclohexylamine in methanol and subsequent fractionated precipitation with diethyl ether.

The bromination of 1-naphtholphthalein mono-phosphates of general formula (I), wherein $R^1$ and $R^2$ are hydrogen atoms and $M^1$ and $M^2$ have the above-given meanings, in diethyl ether gives a mixture of the corresponding 2-monobromo and 2,2′-dibromo compounds of general formula (I), wherein $R^1$ and $R^2$ are hydrogen and/or bromine atoms. There are hereby preferably formed the monobromo-substituted compounds of general formula (I) with bromine in the ortho-position to the phosphate group.

By halogen in the definitions of $R^1$ to $R^5$ is to be understood fluorine, chlorine, bromine or iodine, chlorine and bromine being preferred.

By alkali metal cation in the definition of $M^1$ and $M^2$ is to be understood the lithium, sodium and potassium ion, the lithium and sodium ion being preferred.

The alkaline earth metal cation in the definition of $M^1$ and $M^2$ means the magnesium, calcium or barium ion, the calcium ion being preferred.

The alkyl grouping in the tetraalkylammonium cation and the alkanol grouping in the alkanolammonium cation in the definition of $M^1$ and $M^2$ contains up to 5 and preferably 1 or 2 carbon atoms.

By alkylaryl radicals in the definition of $R^3$ and $R^4$ are to be understood radicals which consist of carbon chains with up to 3 and preferably 1 or 2 carbon atoms and an aromatic radical, preferably the phenyl radical, the benzyl radical here being preferred.

The present invention is also concerned with the use of the new 1-naphtholphthalein monophosphates of general formula (I) for the determination of the activity of alkaline phosphatases.

The use of 1-naphtholphthalein monophosphates as substrates for alkaline phosphatase gives rise to distinctly more sensitive Ap test systems than those previously known. The new substrates can be used with advantage for the determination of the activity of alkaline phosphatases not only in the biochemical but also in the clinical-chemical field.

Because of their good solubility in aqueous media in the pH range of from 10 to 11, the new monophosphate substrates have a high reactivity and a short lag phase in photometric phosphatase tests. This involves the following advantages:
(a) lowering of the detection limit,
(b) short reaction times and
(c) small use of sample and thus also smaller disturbance by other sample components.

Furthermore, because of the large Stokes displacement occurring in the case of the liberated anions, the new substrates show only a slight overlapping with the increase of the absorption, to be monitored photometrically, of the anion resulting in the case of the enzymatic hydrolysis.

Surprisingly, the formation of the red-violet to blue colored anions ($\lambda_{max}$650 nm) already takes place under weakly alkaline conditions (for example at pH 8). It is hereby possible, for the first time, to determine the activity of alkaline phosphatases photometrically in the lower visible spectral range (650 to 670 nm) by continuous measurement in the weakly alkaline pH range with such a high detection sensitivity as was hitherto only possible with more time-consuming non-continuous processes and, at the same time, to eliminate disturbances by sample components, such as bilirubin and other haemolysis products, which do not absorb in this wavelength range, and by insoluble components which cause turbidity.

The 1-naphtholphthalein monophosphates according to the present invention can be used as enzyme substrates for the determination of AP activities in the most varied body fluids (samples), for example blood, serum, plasma, urine, saliva and the ultrafiltrates thereof, as well as in tissue extracts.

The determination of the alkaline phosphatase with the substrates according to the present invention can take place in a concentration range of from 1.0 to 20.0 mM. In the scope of the process according to the present invention, there is advantageously used a concentration of 7.0 to 8.0 mM of 1-naphtholphthalein monophosphate of general formula (I).

The 1-naphtholphthalein monophosphates of general formula (I) can also be used for immunological methods of determination in which alkaline phosphatase is used as indicator enzyme, the activity of which must be determined after carrying out the immunological reaction. Such immunological methods of determination with enzymatic indicator reaction are known to the expert as enzyme immunoassays. These methods serve for the determination of the concentration of proteins, polysaccharides, hormones, pharmaceuticals and other low molecular weight substances in the range of from $10^{-5}$ to $10^{-12}$ mole/liter. Depending upon the requirement of phase separation steps, a distinction is made between a homogeneous and a heterogeneous carrying out of the test. A further subdivision into competitive and non-competitive test principles can also be made.

However, all test principles work with enzyme-antigen or enzyme-antibody conjugates. The enzymatic indicator reaction is common to all enzyme immunoassays.

Alkaline phosphatase is an indicator enzyme which can be used for such purposes. The determination of the alkaline phosphatase in such enzyme immunoassays usually takes place by adding an appropriate AP substrate which is cleaved enzymatically and measured photometrically in the usual way.

Consequently, an improvement of the AP test system also gives rise to considerable advantages in the case of such enzyme immunoassays:
1. The higher sensitivity here also makes possible a further lowering of the limit of detection, short reaction times and small use of sample and thus also smaller disturbances due to other sample components.
2. In the case of certain ways of carrying out reactions, the more favourable measurement wavelength reduces the susceptibility of the method to disturbance due to insoluble components, for example by turbidities.

The present invention is also concerned with diagnostic agents for the determination of the activity of alkaline phosphatases which contain the new 1-naphtholphthalein monophosphates of general formula (I).

Besides containing at least one of the substrates of generally formula (I) according to the present invention, the diagnostic agent contains an appropriate buffer system, consisting of an aminoalcohol, for example N-methyl-D-Glucamine hydrochloride, diethanolamine hydrochloride, triethanolamine hydrochloride and/or 2-amino-2-methylpropan-1-ol hydrochloride, and optionally further substances with buffering properties in the pH range necessary for the AP determination, as well as possibly further appropriate additive materials used for such diagnostic agents, for example wetting agents, stabilisers and the like. The diagnostic agent can be in the form of a solution, possibly buffered to the desired pH value, as a lyophilisate, as a powder mixture or as a reagent tablet or it can be applied to an absorbent carrier or be present in an open film.

The diagnostic agent according to the present invention in the form of a solution preferably contains all the reagents needed for the test. As solvent, there can be used water or a mixture of water with a water-soluble organic solvent, for example methanol, ethanol, acetone, dimethylformamide, dioxan or glycol. For reasons of storage stability, it can be advantageous to divide up the reagents needed for the test into two or more solutions which are first mixed when carrying out the actual investigation.

For the preparation of the diagnostic agent in the form of a lyophilisate with a total weight of from about 5 to 20 mg. and preferably of about 10 mg., a solution is dried which contains, besides all of the reagents needed for the test, conventional structure formers, for example polyvinylpyrrolidone, and possibly further filler materials, for example mannitol, sorbitol or xylitol.

A diagnostic agent in the form of a powder mixture or reagent tablet can be prepared by mixing the components of the test with conventional galenical additive materials and then granulating. Additive materials of this type includes, for example, carbohydrates, such as mono-, oligo- or polysaccharide, or sugar alcohols, such as mannitol, sorbitol and xylitol, and other soluble inert compounds, such as polyethylene glycols and polyvinylpyrrolidone. In general, the powder mixtures or reagent tablets have an end weight of about 30 to 200 mg. and preferably of from 50 to 80 mg.

For the preparation of the diagnostic agent in the form of a test strip, an absorbent carrier, preferably filter paper, cellulose or synthetic resin fleece, is impregnated with solutions of the necessary reagents usually employed for the production of test strips in readily volatile solvents, for example water, methanol, ethanol or acetone. This can take place in one impregnation step. However, it is often advantageous to carry out the impregnation in several stages in which solutions are used each of which contains a part of the components of the diagnostic agent. Thus, for example, in a first step, impregnation can be carried out with an aqueous solution which contains the buffer and other water-soluble additive materials and then, in a second step, with a solution which contains an alkaline phosphatase substrate according to the present invention in a concentration of from 5 to 20 mMole/liter and preferably of from 7 to 8 mMole/liter.

Furthermore, for the production of the diagnostic agent in the form of a test strip, there can be used an open film in which are contained, besides a film former and pigments, a substrate, buffer and other additive materials conventionally used for diagnostic agents. The naphtholphthalein monophosphates of general formula (I) are hereby used in a concentration of from 2 to 20 mM and preferably in a concentration of from 7.5 to 11.3 mM.

The finished test papers and test films can be used as such or are stuck in known manner on to carrier films or preferably sealed between synthetic resins and fine meshworks according to Federal Republic of Germany Patent Specification No. 21 18 455 and brought into contact with the body fluid to be investigated, for example blood, plasma or serum.

The following Examples show some of the numerous process variants which can be used for the synthesis of the compounds according to the present invention, as well as, by way of example, the use of the new 1-naphtholphthalein monophosphates for the determination of the activity of alkaline phosphatase.

The preparation of the substrates and intermediate products of the following general formula:

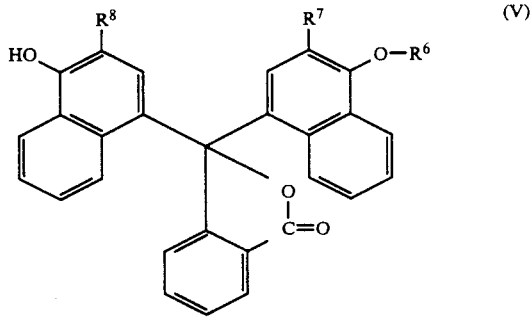

(V)

| | |
|---|---|
| (1) $R^6 = PO_3H_2$; $R^7 = R^8 = H$; | M.W. 498.5 |
| (2) $R^6 = PO_3H_2$; $R^7 = Br$; $R^8 = H$ | M.W. 577.3 |
| (3) $R^6 = PO_3H_2$; $R^7 = R^8 = Br$ | M.W. 656.2 |
| (4) $R^6 = H$; $R^7 = Br$; $R^8 = H$ | M.W. 497.4 |
| (5) $R^6 = H$; $R^7 = R^8 = Br$ | M.W. 576.3 | is explained in more detail in the following Examples.

EXAMPLE 1

1-Naphtholphthalein monophosphate (1)

Phosphorus oxychloride method 6.27 g (0.015 mole) 1- Naphtholphthalein are introduced into a mixture of 25 ml. anhydrous tetrahydrofuran and 1ml. (0.014 mole) dry pryidine, mixed, while stirring, with 1.5 ml. (0.015 mole) phosphorus oxychloride and heated under reflux for 1 hour. Thereafter, 100 ml. 2N hydrochloric acid are added to the reaction mixture which is then heated to 70° C. for 15 minutes, a dark oil thereby separating out. This is separated off and again heated twice for 10 minutes to 70° C. with, in each case, 50 ml. 2N hydrochloric acid, separated off, dropped into 150 ml. water and adjusted to pH 10.3 by the addition of a concentrated aqueous solution of sodium hydroxide. The dark green solution is shaken once with 125 ml. n-butanol/ligroin (1/1 v/v), once with 100 ml. n-butanol/ligroin (1/3 v/v) and once with 100 ml. ligroin. Thereafter, the aqueous phase is adjusted with concentrated hydrochloric acid to pH 7.3 and extracted three times with, in each case, 100 ml. ethyl acetate. The aqueous phase is evaporated to dryness in a rotary evaporator, 2 g. of a brown, amorphous monophosphate thereby being obtained. The crude product is separated on a silica gel 60 column (height 80 cm., diameter 4.5 cm.) with a mixture of chloroform/methanol/methyl ethyl ketone/acetic acid/water (75/35/25/5/9 v/v/v/v/v), there being obtained 1.05 g. of brownish, amorphous 1-naphtholphthalein monophosphate. Yield 14.1% of theory; m.p. 226° C. M.W. 498.5.

$R_f = 0.43$ in the above-mentioned elution agent.

EXAMPLE 2

1-Naphtholphthalein monophosphate (1)

Dibenzyl phosphite method 83.6 g. (0.2 mole) 1-Naphtholphthalein are dissolved in 840 ml. anhydrous tetrahydrofuran, 40 ml. (0.4 mole) dry carbon tetrachloride are added thereto at ambient temperature and thereafter, within the course of 20 minutes, 39.6 ml. (0.18 mole) dibenzyl phosphite and 82.8 ml. (0.6 mole) dry triethylamine are added dropwise thereto, the temperature thereby increasing to 41°

C. The reaction mixture is stirred for 17 hours at ambient temperature, triethylammonium chloride thereby separating out. The undissolved material is filtered off via a fluted filter paper and the filtrate evaporated on a rotary evaporator. The residue of 159 g. of dark oil is dissolved in 400 ml. chloroform/methanol (9/1 v/v) and purified on a silica gel 60 column (height 120 cm., diameter 7.5 cm.). Upon evaporating the appropriate fractions, there are obtained 72.4 g. of a slightly contaminated dark oil which, by renewed application to a silica gel 60 column (height 120 cm., diameter 7.5 cm.) and elution with chloroform/methanol (29.1 v/v), is obtained in a TLC-uniform state.

The so purified 38.2 g. of amorphous red foam of the dibenzyl ester ($R_f=0.4$; elution agent chloroform/methanol 29/1 v/v) is hydrogenated in a mixture of 500 ml. methanol/dioxan (1/1 v/v) with the addition of 1 g. palladium oxide for 4.5 hours at 5 atmospheres and 25° C. After filtering off the catalyst with suction, the yellow solution obtained is evaporated to dryness on a rotary evaporator. There are obtained 26.7 g. of orange-coloured, amorphous product. This is purified on a silica gel 60 column height 120 cm., diameter 7.5 cm.) with the elution agent chloroform/methanol/methyl ethyl ketone/acetic acid/water (75/35/25/5/9 v/v/v/v/v). The crude product, 19.6 g. of a bright orange-coloured powder, is triturated with 200 ml. diethyl ether and the crystals formed are filtered off with suction, washed with diethyl ether and dried to constant weight for 48 hours at 50° C. over phosphorous pentoxide and potassium hydroxide, there being obtained 17.3 g. 1-naphtholphthalein monophosphate. Yeidl 17.4% of theory: m.p. >250° C.

For the removal of adhering acetic acid, the product is dissolved in 350 ml. concentrated ammonia, mixed with 20 g. HP-20 absorber resin (polystyrene-divinyl-chlorobenxzene resin) and evaporated on a rotary evaporator. The residue is applied to a 1 liter HP-20 column and thereafter eluted with 5 liters of water, 7.5 liters 10% isopropanol and finally with 10% ammonia-containing water. The aqueous ammoniacal solution is evaporated in a vacuum and the residue dried to constant weight, there being obtained 10.5 g. of pure 1-naphtholphtalein monophosphate. Yield 10.7% of theory: m.p.>250° C.

$R_f=0.48$ (elution agent isopropanol/n-butyl acetate/water=50/30/20 v/v/v)

$R_f=0.22$ (elution agent chloroform/methanol/methyl ethylketone/ethyl acetate/water 75/35/25/5/9 v/v/v/v/v).

EXAMPLE 3

1-Naphtholphthalein monophosphate (1)

Dibenzyl phosphite phase transfer catalysis

In a 500 ml. three-necked flask equipped with a stirrer, thermometer and dropping funnel, 2.6 ml. (0.02 mole triethylamine are added to a solution of 11 ml. (0.05 mole) dibenzyl phosphite in 100 ml. dry chloroform and 17 ml. carbon tetrachloride and stirred for 1 hour at ambient temperature. 20.8 g. (0.05 mole) 1-Naphtholphthalein (90% by gas chromatography) and 3.23 g. (0.01 mole) tetrabutylammonium bromide are then added thereto and a solution of 53.3 g. (0.4 mole) potassium carbonate in 100 ml. water added dropwise thereto over the course of 10 minutes, while stirring. After further stirring for 1 hour, the organic phase is separated off, extracted three times with, in each case, 150 ml. 1N aqueous sodium hydroxide solution and three times with, in each case, 1550 ml. water, dried over anhydrous sodium sulphate and evaporated on a rotary evaporator. There are obtained 19.1 g. of brown oil. $R_f=0.4$ (elution agent chloroform/methanol 29/1 v/v, TLC silica gel 60 Merck).

This material is dissolved in 300 ml. methanol/dioxan (1/1 v/v) and, after the addition of 1.5 g. 10% palladium/charcoal, hydrogenated, the take up of hydrogen being ended after 2 hours. After filtering off the catalyst with suction, the reaction solution is evaporated, there being obtained 15.4 g. of red resin. This is purified on a silica gel 60 column (height 103 cm., diameter 5.5 cm.) with chloroform/methanol/methyl ethyl ketone/glacial acetic acid/water 75/35/25/5/9 v/v/v/v/v). The TLC-pure fractions are evaporated to give 7.3 g. of orange-red resin, by the addition of 100 ml. diethyl ether and triturating, there are obtained, after filtering off with suction, washing with diethyl ether and drying for 24 hours at ambient temperature, 6.4 g. of a pale orange-coloured amorphous powder. Yield 25.6% of theory; m.p.>250° C. $R_f=0.48$ (elution agent isopropanol/n-butyl acetate/water 50/30/20 v/v/v, TLC HPTLC finished plate: silica gel 60 F 254, Merck).

$R_f=0.32$ (elution agent chloroform/methanol/methyl ethyl ketone/glacial acetic acid/water 75/35/25/5/9 v/v/v/v/v).

The product prepared according to Examples 1 to 3 can be converted with AP in the presence of borate buffer (pH 10.3) into 1-naphtholphthalein ($\lambda_{max}=650$ nm; $\epsilon=30,300$ l/mole.cm.).

EXAMPLE 4

2-Monobromo-1-naphtholphthalein monophosphate (2)

0.4 ml. (0.008 mole) Bromine in 10 ml. diethyl ether is added dropwise, while stirring, and in the course of 10 minutes at 0° C. to a suspension of 2 g. (0.004 mole) 1-naphtholphthalein monophosphate in 50 ml. diethyl ether. The reaction mixture is further stirred for 1 hour at 0° to 5° C., the diethyl ether is decanted off from the oily reaction product and the residue is stirred with 30 ml. ligroin. After filtering off with suction and drying over a molecular sieve, there are obtained 2 g. of beige-coloured 2-monobromo-1-naphtholphthalein monophosphate. Yield 86.6% of theory; m.p. >160° C. (decomp.); M.W. 577.4.

$R_f=0.32$ (elution agent chloroform/methanol/methyl ethyl ketone/water 75/35/25/9, TLC silica gel plate 60 Merck).

EXAMPLE 5

2,2'-Dibromo-1-naphtholphthalein monophosphate (3)

There is used the procedure described in the preceding example but with a mole ratio of 1-naphtholphthalein monophosphate/bromine of 1:3. Besides the monobromo compound, there is obtained the desired 2,2'-dibromo-1-naphtholphthalein monophosphate. Separation takes place on a silica gel 60 column (height 68 cm., diameter 3.5 cm.; elution agent isopropanol/n-butyl acetate/water 50/30/20 v/v/v), there being obtained 0.61 g. of beige-coloured, crystalline 2,2'-dibromo-1-naphtholphthalein monophosphate; yield 23% of theory; m.p. >240° C. (decomp.); M.W. 656.2.

$R_f=0.25$ (elution agent chloroform/methanol/methyl ethyl ketone/water=75/35/25/9 v/v/v/v TLC silicia gel 60 Merck).

The compounds 2-monobromo- and 2,2'-dibromo-1-naphtholphthalein monophosphate, prepared according to Examples 4 and 5, can be cleaved in methanolic solution in the presence of borate buffer and/or of an amino-alcohol (pH 10.5) with alkaline phosphatase, 2-monobromo-1-naphtholphthalein ($\lambda_{max.}=655$ nm., $\epsilon=25,300$ 1/mole.cm.) and 2,2'-dibromo-1-naphtholphthalein ($\lambda_{max.}=670$ nm, $\epsilon=27,800$ 1/mole.cm.) thereby being formed.

EXAMPLE 6

2Monobromo- and 2,2'-dibromo-1-naphtholphthalein (4) and (5)

In a 250 ml. three-necked flask equipped with a stirrer and thermometer are dissolved 4.18 g. (0.01 mole) 1-naphtholphthalein in 100 ml. diethylether and a solution of 2.4 g. (0.77 ml., 0.015 mole) bromine in 80 ml. diethyl ether added dropwise thereto to 0° C. while stirring, within the course of 2 hours. After leaving to stand overnight, the reaction mixture is evaporated in a vacuum to give 5.5 g. of a mixture of approximately equal parts of mono- and dibromo compound. Column chromatographic separation on silica gel 60 Merck takes place with toluene/ethyl acetate (15/1 v/v) or with isopropanol/n-butyl acetate/water (50/30/20 v/v/v), there being obtained 2.6 g. of beige-coloured, crystalline dibromo compound. Yield 45% of theory; m.p. >245° C. (decomp.). $R_f=0.5$ (elution agent toluene-/ethyl acetate 5/1 v/v). $\lambda_{max.}=670$ nm
and 1.6 g. beige-coloured, powdery monobromo compound, yield 30% of theory; m.p. >240° C. (decomp.) $R_f=0.32$ (elution agent toluene/ethyl acetate 5/1 v/v) $\lambda_{max.}=655$ nm.

EXAMPLE 7

Determination of the activity of alkaline phosphatase by extinction photometry in a cuvette (a) Preparation of the solutions used:
Buffer solution:

| N-methyl-D-glucamine | 1 mole/liter |
|---|---|
| pH value (adjusted with 1N hydrochloric acid) | 10.2 |

Reagent solution 1:
7.5 mMole/liter 1-naphtholphthalein monophosphate sodium salt are dissolved in the above-described buffer solution. The pH value is monitored (25° C.).

Reagent solution 2:
7.5 mMole/liter 2-bromo-1-naphtholphthalein monophosphate sodium salt are dissolved in the above-described buffer solution. The pH value is monitored (25° C.).

Reagent solution 3:
7.5 mMole/liter 2,2'-dibrom-1-naphtholphthalein monophosphate sodium salt are dissolved in the above-described buffer solution. The pH value is monitored (25° C.).

The substrate concentration and pH values are to be optimised for each substrate used. Therefore, quite knowingly, different values for substrate concentrations or pH values can occur in the case of the individual reagent solutions. The finished reagent solution is stable at ambient temperature for 8 hours and at 37° C. for 1.5 hours.

Enzyme solution

Commercially available alkaline phosphatase from calf intestine is dissolved in the above-mentioned buffer solution. The activity of this solution is about 3000 U/ml. (referred to the manufacturer's data).

Sample solution.

The sample, for example centrifuged blood, plasma or serum, is, if necessary, diluted with the buffer solution.

(b) Measurement.

The measurement takes place photometrically at the particular given wavelength:

3 ml. of reagent are mixed in a 1 cm. cuvette at 37° C. with 50 µl. of the appropriately diluted sample solution or with 50 µl. of enzyme solution. From the extinction change per unit time in $\Delta E$/min. and the chosen dilution, there is calculated the activity of the enzyme solution or of the sample in known manner. For a resulting activity in the cuvette of 50 U/liter, there is found a $\Delta E$/min. of about 220 mE.

| reagent No. | measurement wavelength (nm) |
|---|---|
| 1 | 650 |
| 2 | 655 |
| 3 | 670 |

EXAMPLE 8

Determination of the activity of alkaline phosphatase by reflection photometry of test strips (a) Preparation of test strips with absorbent reagent carrier.

Impregnation solution 1:

| N-methyl-D-glucamine | 2 mole/liter |
|---|---|
| magnesium chloride | 1 mMole/liter |
| zinc chloride | 15 µmole/liter |
| 1-naphtholphthalein monophosphate | 7.5 mMole/liter |
| pH value (adjusted with 1N hydrochloric acid) | 10.2 (25° C.) |

Impregnation solution 2:

| N-methyl-D-glucamine | 2 mole/liter |
|---|---|
| magnesium chloride | 1 mMole/liter |
| zinc chloride | 15 µmole/liter |
| 2-bromo-1-naphtholphthalein monophosphate | 7.5 mMole/liter |
| pH value (adjusted with 1N hydrochloric acid) | 10.2 (25° C.) |

Impregnation solution 3:

| N-methyl-D-glucamine | 2 mole/liter |
|---|---|
| magnesium chloride | 1 mMole/liter |
| zinc chloride | 15 µmole/liter |
| 2,2'-dibromo-1-naphtholphthalein monophosphate | 7.5 mMole/liter |
| pH value (adjusted with 1N hydrochloric acid) | 10.2 (25° C.) |

An absorbent carrier (paper, fleece or synthetic resin fabric) is impregnated with an impregnation solution in known manner. The absorbent reagent carrier thus obtained is fixed in known manner (see Federal Republic of Germany Patent Specification No. 24 36 598) on to a synthetic resin strip which, in conjunction with a reflection photometer, for example Reflotron, permits the determination of the AP activity.

(b) Production of test strips with absorbent reagent film.

Buffer solution:

| N-methyl-D-glucamine | 2 mole/liter |
|---|---|
| pH value | 11.8 |

Film coating mixture.

The buffer solution is mixed in a ratio of 1:1 with a 10% by volume aqueous solution of polyvinyl alcohol (Mowiol 26/88). Subsequently, the pH value is adjusted to 10.5 with 1N hydrochloric acid.

Film coating mass 1.

100 g. Silica (Celaton MW 25) and 3 g. 1-naphtholphthalein monophosphate are introduced, while stirring, into 500 g. of the film coating mixture.

Film coating mass 2.

100 g. Silica (Celaton MW 25) and 3.5 g. (2-bromo-1-naphtholphthalein monophosphate are introduced, while stirring, into 500 g. of the film coating mixture.

Film coating mass 3.

100 g. Silica (Celaton MW 25) and 4 g. 2,2'-dibromo-1-naphtholphthalein monophosphate are introduced, while stirring, into 500 g. of the film coating mixture.

The individual air bubble-free coating masses are applied in a wet thickness of 200 to 500 μm. and preferably of 300 μm., for example by means of a rake, to the synthetic resin film. Subsequently, drying is carried out for 30 minutes at 60° C. in a circulating air drying cabinet.

The so obtained reagent film carrier is fixed in known manner (see Federal Republic of Germany Patent Specification No. 31 30 749) on to a synthetic resin strip which, as in the case of (a), permits the determination of the AP activity.

(c) Measurement

The test strips produced according to (a) and (b) can be measured in an appropriate reflection photometer, for example Reflotron. The reaction is here started in known manner by making contact between sample and paper or film reagent carrier. The AP activity in the sample is determined from the chronological change of the remission at the particular given wavelength:

| impregnation solution No. | film coating mass No. | measurement wavelength (nm) |
|---|---|---|
| 1 | 1 | 650 |
| 2 | 2 | 655 |
| 3 | 3 | 670 |

Various embodiments of the compositions and methods described and claimed herein will of course be evident to the skilled artisan. The examples given herein are in no way to be construed as limitative of the broad disclosure.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. 1-Naphtholphthalein monophosphates of the formula

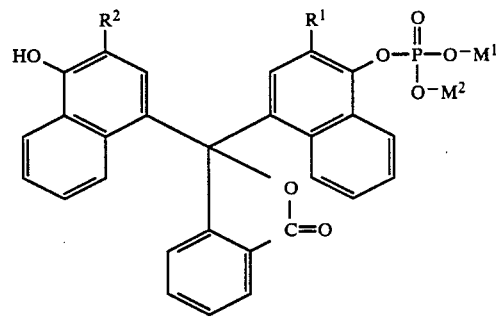

wherein
each of $R^1$ and $R^2$ is hydrogen or halogen, and
each of $M^1$ and $M^2$ is a proton or an alkali metal, alkaline earth metal, ammonium, dicyclohexylammonium, tetraalkylammonium or alkanolammonium cation,
and the tautomeric transformation products thereof.

2. 1-Naphtholphthalein monophosphate according to claim 1, wherein $R^1$ and $R^2$ are both hydrogen, and $M^1$ and $M^2$ are both protons.

3. 1-Naphtholphthalein monophosphate according to claim 1, wherein $R^1$ is a bromine, $R^2$ is hydrogen, and $M^1$ and $M^2$ are both protons.

4. 1-Naphtholphthalein monophosphate according to claim 1, wherein $R^1$ and $R^2$ are both bromine, and $M^1$ and $M^2$ are both protons.

5. A diagnostic agent for the determination of alkaline phosphotase comprising (1) as a chromogenic substrate, a 1-naphtholphthalein monophosphate compound of the formula

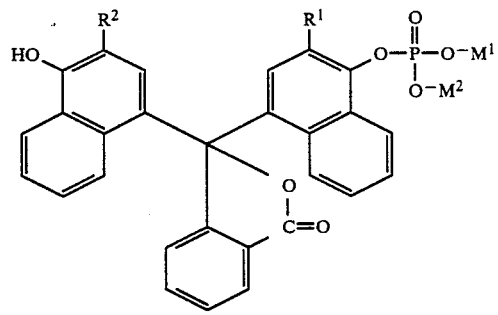

in which
each of $R^1$ and $R^2$ is hydrogen or halogen, and
each of $M^1$ and $M^2$ is a proton or an alkali metal, alkaline earth metal, ammonium, dicyclohexylammonium, tetraalkylammonium or alkanolammonium cations, or a tautomeric transformation product thereof, and
(2) a buffering substance.

6. A diagnostic agent according to claim 5 in which, in the compound, each of $R^1$ and $R^2$ is hydrogen or bromine, and $M^1$ and $M^2$ are both protons.

7. A diagnostic agent according to claim 5 which additionally comprises one or more wetting agents, swelling agents, film formers, structure formers and/or pigments.

* * * * *